(12) United States Patent
Achilefu et al.

(10) Patent No.: US 8,344,158 B2
(45) Date of Patent: Jan. 1, 2013

(54) FLUORESCENT POLYMETHINE CYANINE DYES

(75) Inventors: Samuel Achilefu, St. Louis, MO (US); Hyeran Lee, St. Louis, MO (US); John Christian Mason, deceased, St. Louis, MO (US); Hyeran Lee, legal representative, St. Louis, MO (US)

(73) Assignee: Washington University, St. Louis, MO (US)

( * ) Notice: Subject to any disclaimer, the term of this patent is extended or adjusted under 35 U.S.C. 154(b) by 1004 days.

(21) Appl. No.: 12/192,480

(22) Filed: Aug. 15, 2008

(65) Prior Publication Data
US 2009/0124792 A1    May 14, 2009

Related U.S. Application Data

(60) Provisional application No. 60/955,908, filed on Aug. 15, 2007.

(51) Int. Cl.
*C09B 23/08*     (2006.01)
*C12Q 1/68*     (2006.01)

(52) U.S. Cl. ........................ 548/427; 548/455

(58) Field of Classification Search .............. 430/270.21
See application file for complete search history.

(56) References Cited

U.S. PATENT DOCUMENTS

| | | | |
|---|---|---|---|
| 4,987,021 A * | 1/1991 | Kanno et al. | 428/64.8 |
| 5,107,063 A * | 4/1992 | West et al. | 548/455 |
| 5,268,486 A | 12/1993 | Waggoner et al. | |
| 5,290,670 A * | 3/1994 | Delprato et al. | 430/510 |
| 5,508,161 A * | 4/1996 | Miyake et al. | 430/574 |
| 5,589,250 A | 12/1996 | Asai | |
| 5,955,224 A * | 9/1999 | Caspar et al. | 430/17 |
| 6,747,159 B2 * | 6/2004 | Caputo et al. | 548/414 |
| 7,172,907 B2 | 2/2007 | Chen et al. | |
| 7,547,721 B1 * | 6/2009 | Miwa et al. | 514/414 |
| 2004/0014981 A1 | 1/2004 | Lugade et al. | |
| 2007/0042398 A1 | 2/2007 | Peng et al. | |
| 2009/0214436 A1* | 8/2009 | Achilefu et al. | 424/9.6 |
| 2010/0215585 A1* | 8/2010 | Frangioni | 424/9.6 |
| 2010/0323389 A1* | 12/2010 | Xu et al. | 435/29 |

FOREIGN PATENT DOCUMENTS

| | | | |
|---|---|---|---|
| JP | 06-145539 | * | 5/1994 |
| WO | WO 00/16810 | * | 3/2000 |
| WO | WO 01/43781 | * | 6/2001 |
| WO | WO 2004/065491 | * | 8/2004 |
| WO | WO 2008/017074 | * | 2/2008 |

OTHER PUBLICATIONS

Lee, Hyeran et al., "Heptamethine Cyanine Dyes with a Robust C-C Bond at the Central Position of the Chromophore", Journal of Organic Chemistry, 71, 7862-7865, publication date web Aug. 29, 2006.*

Lee, Hyeran et al, "Synthesis and Spectral Properties of Near-Infrared Aminophenyl-, Hydroxyphenyl- and Phenyl-Substituted Heptamethine Cyanines", Journal of Organic Chemistry, 73, 723-725, publication date web Dec. 21, 2007.*

Registry No. 70446-35-4, entered into Registry file on STN on Nov. 16, 1984.*

Lenhard, J. R. et al., "Electrochemistry and Electronic Spectra of Cyanine Dye Radicals in Acetonitrile", Journal of Physical Chemistry, 97, 4916-4925, 1993.*

Hilderbrand, Scott A. et al., "Monofunctional Near-Infrared Fluorochromes for Imaging Applications", Bioconjugate Chemistry, 16(5), 1275-1281, 2005.*

Bouteiller, Cedric et al., "Novel Water-Soluble Near-Infrared Cyanine Dyes: Synthesis, Spectral Properties, and Use in the Preparation of Internally Quenched Fluorescent Probes", Bioconjugate Chemistry, 18, 1303-1317, publication date web Jun. 21, 2007.*

Lee, Hyeran et al "Heptamethine Cyanine Dyes with a Robust C-C Bond at the Central Position of the Chromophore", Journal of Organic Chemistry, 71(20), 7862-7865, published on web Aug. 29, 2006.*

Berezin, Mikhail Y. et al., "Ratiometric Analysis of Fluorescence Lifetime for Probing Binding Sites in Albumin with Near-infrared Fluorescent Molecular Probes", Photochemistry and Photobiology, 83(6), 1371-1378, (article published online Jul. 5, 2007).*

Brinkley, M, A Bref Suvey of Methods for Preparng Protein Conjugates with Dyes, Haptens and Cross-Linking Reagents, Bioconjugate Chem, 1992, pp. 2-13, vol. 3.

Braeckmans et al, Three-Dimensional Fluorescence Recovery after Photobleaching with the Confocal Scanning Laser Microscope, Biophysical J., 2003, pp. 2240-2252, vol. 85.

Braga et al, Intracellular Macromolecular Mobility Measured by Fluorescence Recovery after Photobleaching with Confocal Laser Scanning Microscopes, Molecular Biology of the Cell, 2004, pp. 4749-4760, vol. 15.

Haraguchi, T, Live Cell Imaging: Approaches for Studying Protein Dynamics in Living Cells, Cell Structure and Function, 2002, pp. 333-334, vol. 27.

Gordon et al, Analysis of Simulaed and Experimental Fluorescence Recovery After Photobleaching. Data for Two Diffusing Components, Biophysical J., 1995, pp. 766-778, vol. 68.

Lukevits, Catalytic Synthesis and Reactions of Nitrogen Heterocycles, Chemistry of Heterocyclic Compounds, 1994, pp. 1284-1307, 30(11-12).

Non-final Office action from related U.S. Appl. No. 12/370,758 dated Sep. 30, 2011, 12 pgs.

Final Office Action dated May 25, 2012 from related U.S. Appl. No. 12/370,758, 12 pages.

Achilefu, Synergistic effects of light-emitting probes and peptides for targeting and monitoring integrin expression, PNAS, May 31, 2005, pp. 7976-7981, vol. 102, No. 22.

* cited by examiner

*Primary Examiner* — Fiona T Powers
(74) *Attorney, Agent, or Firm* — Polsinelli Shughart PC

(57) ABSTRACT

The invention encompasses fluorescent cyanine dyes and methods of using such dyes. In particular, the invention encompasses near infrared polymethine cyanine dyes.

6 Claims, 6 Drawing Sheets

A

ICG

B

Cypate $R^1 R^2 = (CH=CH)_2-$; $R^1 = SO_3Na$, $R^2 = H$
n = 1, 2

1a: $R^1$ = H, $R^2$ = H, $R^3$ = COOH, n = 1
1b: $R^1R^2$ = -(CH=CH)$_2$-, $R^3$ = H, n = 1
1c: $R^1R^2$ = -(CH=CH)$_2$-, $R^3$ = H, n = 2
1d: $R^1$ = SO$_3$Na, $R^2$ = H, $R^3$ = H, n = 2

2a: $R^1$ = H, $R^2$ = H, $R^3$ = COOH, n = 1
2b: $R^1R^2$ = -(CH=CH)$_2$-, $R^3$ = H, n = 1
2c: $R^1R^2$ = -(CH=CH)$_2$-, $R^3$ = H, n = 2
2d: $R^1$ = SO$_3$Na, $R^2$ = H, $R^3$ = H, n = 2

FLUORESCENT POLYMETHINE CYANINE DYES

CROSS REFERENCE TO RELATED APPLICATIONS

This application claims the priority of U.S. provisional application No. 60/955,908, filed Aug. 15, 2007, hereby incorporated by reference in its entirety.

GOVERNMENTAL RIGHTS

The present invention was supported by the National Institute of Health Grant Nos. R01EB 1430 and R01CA 109754. The United States Government has certain rights in this invention.

FIELD OF THE INVENTION

The invention encompasses stable near-infrared cyanine dyes and methods of using such dyes.

BACKGROUND OF THE INVENTION

Molecules that absorb and emit light in the near-infrared (NIR) wavelengths have become the central focus of numerous analytical, biological, and spectroscopic studies because their spectral, chemical, and biological properties facilitate the detection of minute molecular processes in solutions and living tissues. Using NIR fluorescent technology allows almost the complete elimination of background from auto fluorescence of biomolecules. Also the background from the scattered light from the excitation source is greatly reduced since the scattering intensity is proportional to the inverse fourth power of the wavelength.

Cyanine dyes have been widely used for labeling biomolecules including antibodies, DNA probes, avidin, streptavidin, lipids, biochemical analogs, peptides, and drugs, as well as for a variety of applications including DNA sequencing, DNA microarray, western blotting, flow cytometry analysis, and protein microarrays to name a few. The excellent safety profile of the NIR heptamethine cyanine fluorochrome indocyanine green (ICG) in humans has spurred interest in the development of ICG derivatives, including Cy dyes and cypate for in vivo molecular imaging by NIR optical methods. But the low fluorescence quantum yield, short fluorescence lifetime, propensity to photobleach, and poor chemical stability of these dyes have limited their use in chemical and life sciences.

Attempts to overcome these limitations have led to monofunctional cyanine dyes produced using highly toxic organic solvents resulting in a poor yield and cyanine dye stability concerns. Further, currently available NIR dyes possess a conformationally constrained central meso-chloro cyclohexenyl group, which is functionalized for labeling or available for reaction with diverse molecules by substituting the chloro with heteroatoms such as O, S, and N. These heteroatoms introduce a high degree of chemical and biological instability. The art is in need of stable cyanine dyes that can be produced cost-effectively without the use of toxic solvents.

SUMMARY OF THE INVENTION

One aspect of the present invention encompasses a fluorescent cyanine dye. The dye has two nitrogen atoms that are each independently a part of at least two different heteroaromatic rings. The heteroaromatic rings are joined by a polymethine chain, which comprises a carbocylic ring that is centrally located within the polymethine chain. The carbocylic ring is derivatized with a hydrocarbyl or a substituted hydrocarbyl group at the meso position in a manner such that the dye is substantially fluorescent.

Another aspect of the present invention encompasses a compound. The compound comprises a fluorescent cyanine dye conjugated to a biomolecule. The dye has two nitrogen atoms that are each independently a part of at least two different heteroaromatic rings. The heteroaromatic rings are joined by a polymethine chain, which comprises a carbocylic ring that is centrally located within the polymethine chain. The carbocylic ring is derivatized with a hydrocarbyl or a substituted hydrocarbyl group at the meso position in a manner such that the dye is substantially fluorescent.

Yet another aspect of the present invention encompasses a process for producing a fluorescent cyanine dye. The process comprises, in part, combining a meso-chloro substituted hetamethine cyanine dye, 4-carboxyphenylboric acid, and water, then heating the combination under reflux in the presence of $Pd(PPh_3)_4$, and isolating the resulting fluorescent cyanine dye.

Other aspects and iterations of the invention are described more thoroughly below.

DETAILED DESCRIPTION OF THE INVENTION

Figure 1:
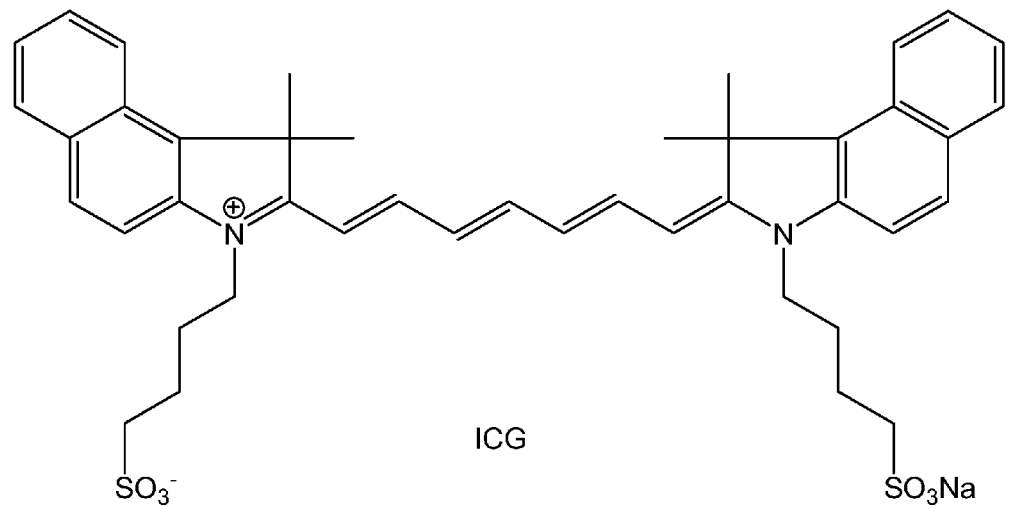
FIG. 1 depicts structures of representative cyanine dyes, near-infrared heptamethine cyanine fluorochrome, indocyanine green (ICG, FIG. 1A) and ICG derivative, cypate (FIG. 1B).
Figure 1:
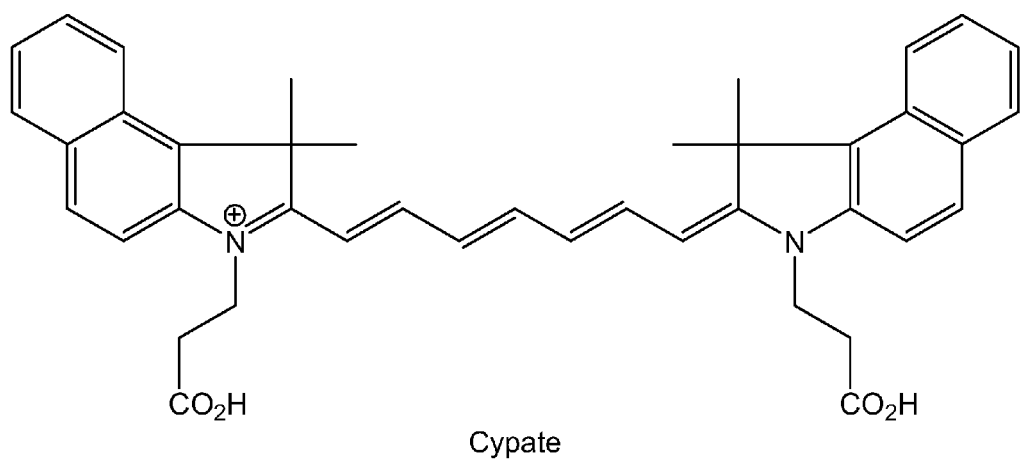

It has been discovered that a C—C bond inserted at the central position of the chromophore of a polymethine cyanine dye structure results in highly fluorescent, monofunctional, water-soluble, near-infrared (NIR) cyanine dye. In particular, utilizing a direct substitution of a meso-chlorine atom in the polymethine chain of heptamethin cyanine dyes to give a C—C bond in the chromophore region offers chemical and biological stability towards the hydrolytic cleavage that commonly occurs with fluorochromes and further optimizes the chemical and photochemical properties of NIR fluorophores. The enhanced stability allows changes observed in spectral properties to be attributed accurately to targeted processes. Accordingly, the present invention provides stable near-infrared heptamethine cyanine dyes and methods of producing such dyes that can be used for imaging, biomedical, and analytical applications.

(I) Fluorescent Cyanine Dyes

The compounds of the invention comprise fluorescent cyanine dyes having two quaternized nitrogen atoms linked by a polymethine chain having a cyclic group centrally located within the chain. The nitrogen atoms are each independently part of a heteroaromatic ring. Non-limiting examples of heteroaromatic rings include imidazole, pyridine, pyrrole, quinoline, and thiazole. In one alternative of this embodiment, the compound comprises a cyanine dye having Formula (I):

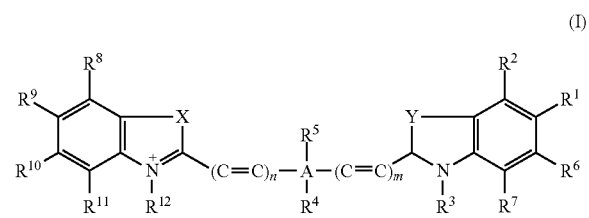

(I)

wherein:
A is a cyclic group selected from a carbocyclic ring, and a heterocyclic ring;
X and Y are independently selected from the group consisting of a heteroatom, an alkyl group, an alkenyl group, and an alkynyl group;
n and m are independent integers from 1 to about 5;
$R^1$, $R^2$, $R^4$, $R^5$, $R^6$, $R^7$, $R^8$, $R^9$, $R^{10}$ and $R^{11}$ are independently selected from the group consisting of functional group, hydrogen, hydrocarbyl, and substituted hydrocarbyl; and
$R^3$ and $R^{12}$ are selected from the group consisting of hydrocarbyl, and substituted hydrocarbyl.

In an exemplary embodiment compounds correspond to Formula (I) wherein:
X and Y are independently selected from the group consisting of sulfur, oxygen, carbon, selenium, nitrogen, and $C(CH_3)_3$;
A is a carbocyclic ring;
n and m are independent integers from 1 to 3; and
$R^1$, $R^2$, $R^3$, $R^4$, $R^5$, $R^6$, $R^7$, $R^8$, $R^9$, $R^{10}$, $R^{11}$, and $R^{12}$, are as described above.

In one alternative embodiment, the compound encompasses a heptamethine cyanine dye having Formula (II):

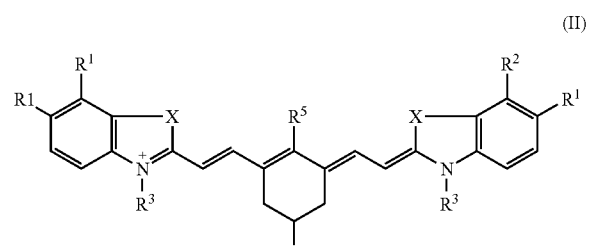

(II)

wherein:
X is selected from the group consisting of a heteroatom, an alkyl group, an alkenyl group, and an alkynyl group;
$R^1$, $R^2$, and $R^4$ are independently selected from the group consisting of hydrogen, hydrocarbyl, and substituted hydrocarbyl; and
$R^3$ and $R^5$ are selected from the group consisting of hydrocarbyl and substituted hydrocarbyl.

In an exemplary embodiment for compounds having Formula (II), X is selected from the group consisting of sulfur, oxygen, carbon, and $C(CH_3)_3$; and $R^1$, $R^2$, $R^3$, $R^4$, and $R^5$ are as described above.

In still another alternative of the invention, the compound is a heptamethine cyanine dye having Formula (III):

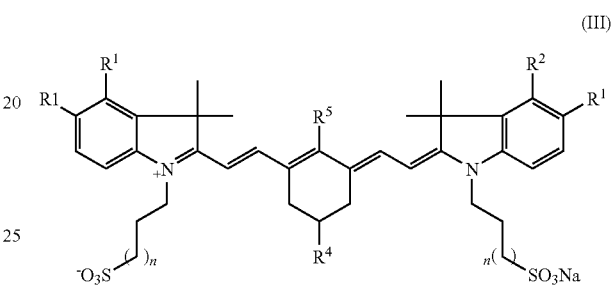

(III)

wherein:
n is an integer from 1 to 10;
$R^1$, and $R^2$, and $R^4$ are independently selected from the group consisting of hydrogen, hydrocarbyl, and substituted hydrocarbyl; and
$R^5$ is selected from the group consisting of hydrocarbyl and substituted hydrocarbyl.

In another embodiment, for compounds having Formula (III), $R^1$ and $R^2$ are $(CH=CH)_2$; n is 1 or 2, and $R^4$ and $R^5$ are as described above.

In yet another embodiment, $R^1$ is $SO_3Na$, $R^2$ is hydrogen; n is 1 or 2; and $R^4$ and $R^5$ are as described above.

For each of the foregoing embodiments, the cyanine dyes of the invention may include one or more reactive groups for coupling the dye compound to a biomolecule. In one embodiment, one or both $R^3$ groups may include a reactive group for coupling the dye compound to a biomolecule. In another embodiment, the $R^5$ group may include a reactive group for coupling the dye compound to a biomolecule. In still another embodiment, one or both $R^3$ groups and the $R^5$ group may include a reactive group for coupling the dye compound to a biomolecule. Suitable non-limiting examples of biomolecules include antigens, steroids, vitamins, drugs, haptens, metabolites, toxins, environmental pollutants, antibodies, DNA, RNA, peptides, proteins, siRNA, miRNA, carbohydrates, lipids, and small molecules. In an exemplary embodiment, the biomolecule is a peptide. The biomolecule may be coupled to the dye compound by methods generally known in the art or by methods described herein.

Alternatively, $R^1$, $R^2$, $R^3$, $R^4$, and $R^5$ may be selected to modify or optimize the physical and/or functional properties of the cyanine dye. $R^1$ and $R^2$ groups may be selected, for example, to modify a physical characteristic of the dye compound selected from the group consisting of water solubility, biodistribution, and spectral elongation. $R^3$ may be selected to modify the water solubility of the dye; and $R^5$ may be selected to provide a pH sensor group.

Exemplary non-limiting examples of cyanine dyes of the invention are shown in Table A.

TABLE A
| Compound Number | Structure |
|---|---|
| A1 | 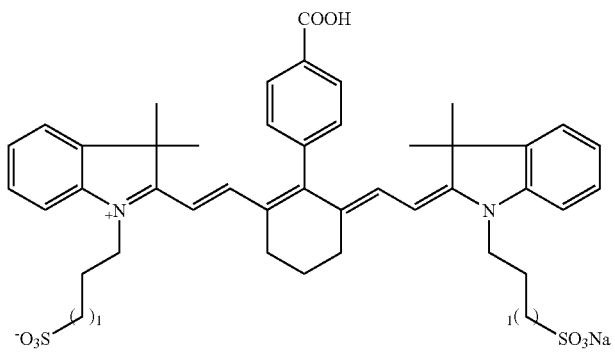 |
| A2 | 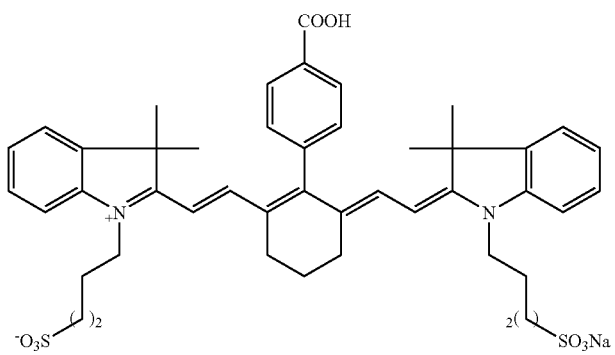 |
| A3 | 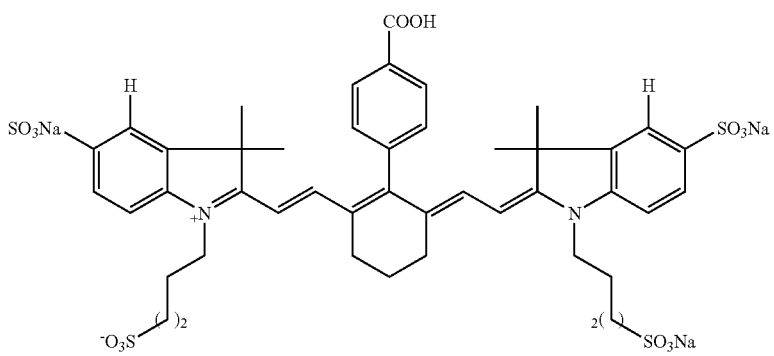 |
| A4-1 | 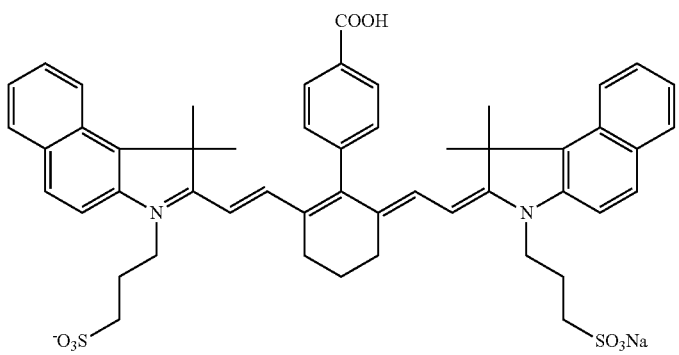 |

TABLE A-continued
| Compound Number | Structure |
| --- | --- |
| A4 | 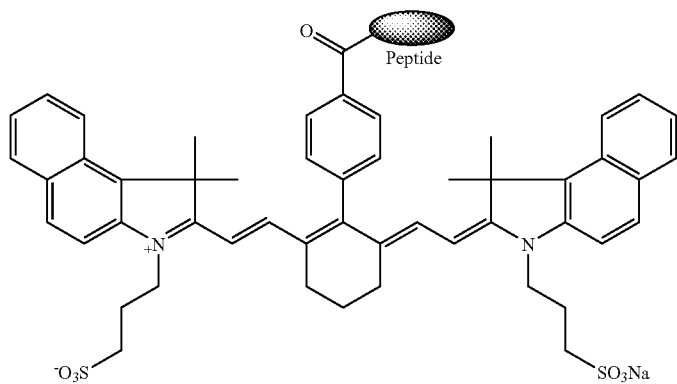 |
| A5 | 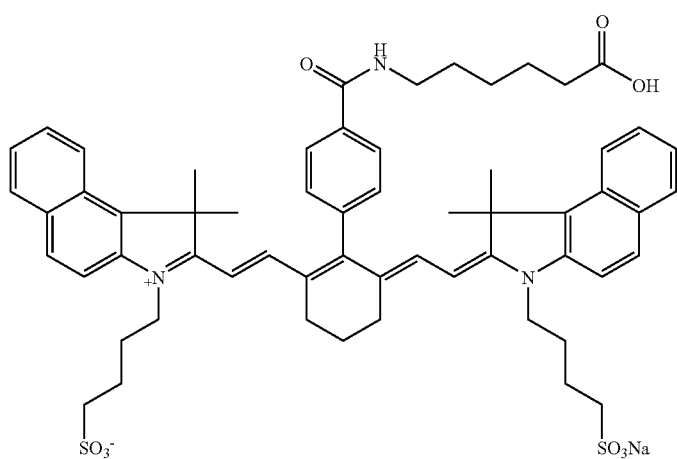 |
| A6 | 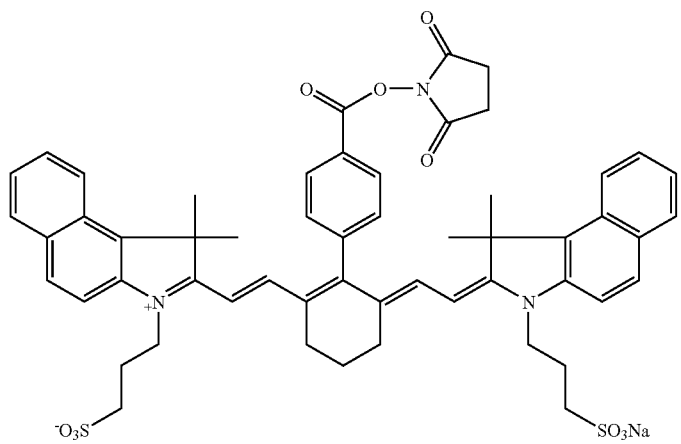 |

TABLE A-continued
| Compound Number | Structure |
|---|---|
| A7 | 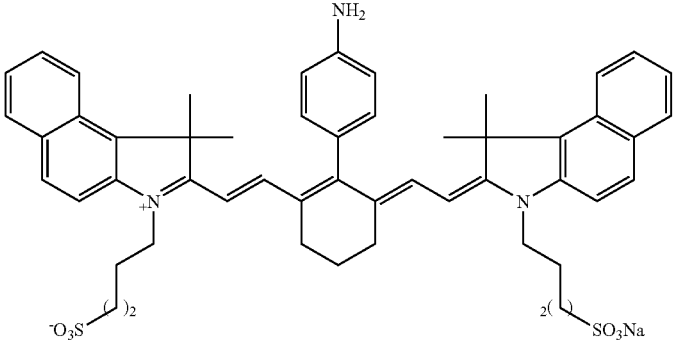 |
| A8 | 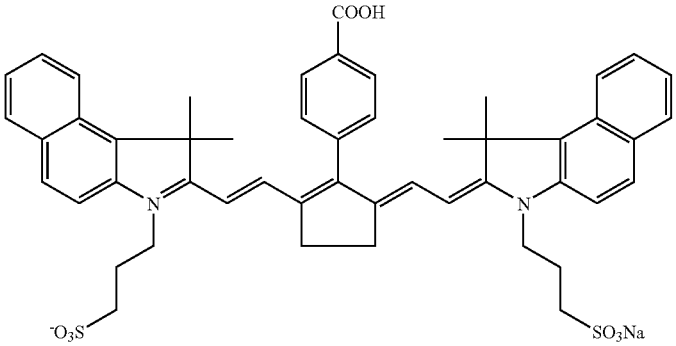 |
| A9 | 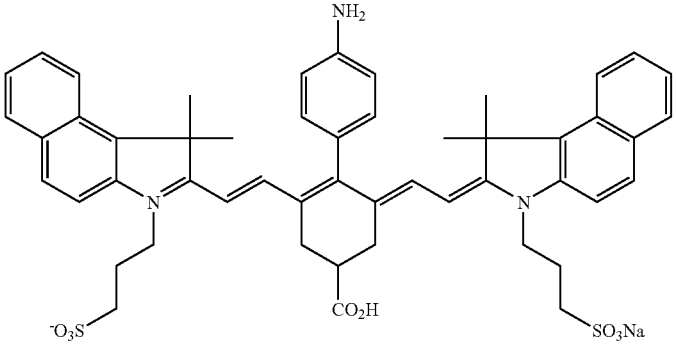 |
| A10 | 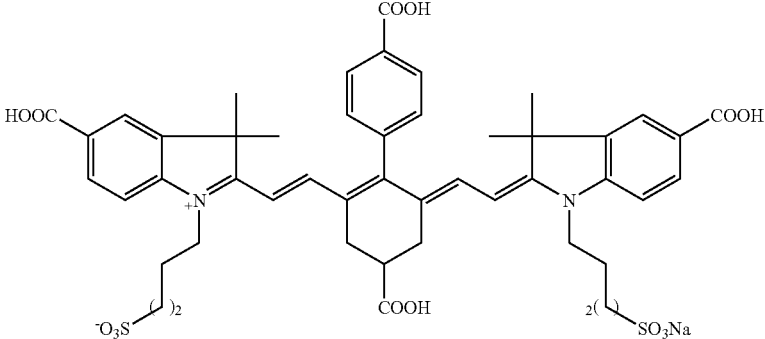 |

The fluorescent cyanine dyes generally have absorption spectra ranging from about 600 nm to about 1000 nm. In an exemplary embodiment, the absorption spectrum is from about 700 nm to about 900 nm. In certain embodiments, the absorption spectra is above about 705 nm, 710 nm, 715 nm, 720 nm, 725 nm, 730 nm, 735 nm, 740 nm, 745 nm, 750 nm, 755 nm, 760 nm, 765 nm, 770 nm, 775 nm, 780 nm, 785 nm, 790 nm, 795 nm, 800 nm, 805 nm, 810 nm, 815 nm, 820 nm, 825 nm, 830 nm, 835 nm, 840 nm, 845 nm, 850 nm, 855 nm, 860 nm, 865 nm, 870 nm, 875 nm, 880 nm, 885 nm, 890 nm, 895 nm, or greater than 900 nm.

(II) Process for Preparing Fluorescent Cyanine Dyes

Figure 5:
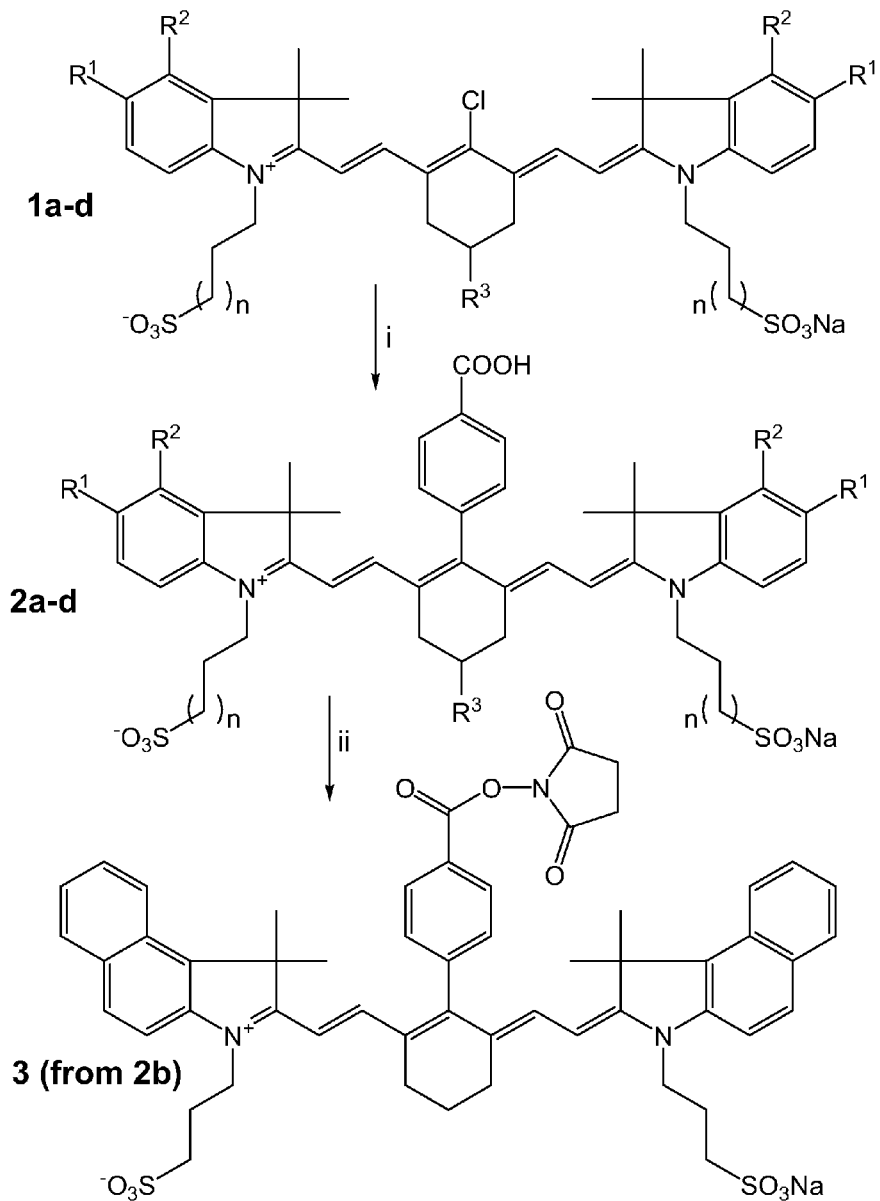
FIG. 5 depicts a schematic of C,C-coupling of Meso-chloro-substituted heptamethine cyanine dyes. The reaction conditions include: (i) $4\text{-}B(OH)2\text{-}C_6H_4\text{—}COOH/Pd(PPh_3)_4/H_2O$, reflux; and (II) N-hydroxysuccinimide/DIC/DMF.

The cyanine dyes may be prepared by methods known in the art including the Suzuki-Miyaura method (see FIG. 5) as described in the Examples. For example, the precursor chloro cyanine dyes indicated in FIG. 5 as 1a-1d and utilized in the C,C-coupling reactions can be efficiently synthesized by a condensation reaction of a heterocyclic base with Vilsmeier-Haack reagents by methods known in the art. Then, separate reactions of chloro-substituted indolium or benz[e]indolium dyes (indicated as 1a-c in FIG. 5) with 4-B(OH)$_2$—C$_6$H$_4$—COOH in the presence of Pd(PPh$_3$)$_4$ using aqueous reaction conditions affords the desired dyes indicated by 2a-c in FIG. 5. Alternatively, the coupling method may also be used with the hydrophilic tetrasulfonate (1d of FIG. 5) under similar reaction conditions to efficiently replace the meso-chlorine atom with a carboxy-functionalized aryl moiety producing compound 2d of FIG. 5. Advantageously, both of the aforementioned processes use water as a solvent. The water-soluble NIR bioconjugatable fluorochromes can be prepared directly in a one-pot procedure from commercially available chloro-substituted dyes such as IR-820. Furthermore, this route offers fluorochromes in an analytically pure form at the gram scale due to purification by simple crystallization. Other purification methods include those in the art which are usually employed in the purification of analogous compounds, such as dissolution, extraction, separation, decantation, filtration, concentration, thin layer chromatography, column chromatography, gas chromatography, high-performance liquid chromatography, distillation, sublimation, crystallization, or a combination thereof. Detailed reaction schemes are delineated in the Examples.

(III) Conjugation of Fluorescent Cyanine Dyes to a Biomolecule

The fluorescent cyanine dyes may be attached to a biomolecule or a ligand to form a conjugated substrate. Attachment may be, for example, by covalent bonding, ionic bonding, dated bonding, hydrogen bonding, and other forms of molecular bonding.

Several types of biomolecules are suitable for conjugation to the cyanine dyes. For example, useful conjugated substrates of the invention include, but are not limited to, conjugates of antigens, small molecules, steroids, vitamins, drugs, haptens, metabolites, toxins, environmental pollutants, amino acids, peptides, proteins, photosensitizers, nucleotides, oligonucleotides, nucleic acids, carbohydrates, lipids, ion-complexing moieties, and non-biological polymers. In one exemplary embodiment, the conjugated substrate is a natural or synthetic amino acid; a natural or synthetic peptide or protein; or an ion-complexing moiety. Preferred peptides include, but are not limited to protease substrates, protein kinase substrates, phosphatase substrates, neuropeptides, cytokines, and toxins. Preferred protein conjugates include enzymes, antibodies, lectins, glycoproteins, histones, alumin, lipoproteins, avidin, streptavidins, protein A, protein G, casein, phycobiliproteins, other fluorescent proteins, hormones, toxins, growth factors, and the like.

The point of attachment of the biomolecule to the cyanine dye can and will vary depending upon the embodiment. In certain embodiments, the point of attachment may be at position $R^4$ of any of the compounds described in (I) above. In another embodiment, the point of attachment may be at position $R^3$ of any of the compounds described in (I) above. In yet another embodiment, the point of attachment may be at position $R^5$ of any of the molecules described in (I) above. It is also envisioned that more than one biomolecule may be conjugated to the cyanine dye. For example, two, three or more than three biomolecules may be conjugated to the cyanine dye.

Several methods of linking dyes to various types of biomolecules are well known in the art. For example, methods for conjugating dyes to a biomolecule are described in R. Haughland, *The Handbook_A Guide to Fluorescent Probes and Labeling Technologies*, 9$^{th}$ Ed., 2002, Molecular Probes, Inc. and the references cited therein; and Brindley, 1992, *Bioconjugate Chem.* 3:2, which are all incorporated herein by reference. By way of example, a cyanine dye may be covalently attached to DNA or RNA via one or more purine or pyrimidine bases through an amide, ester, ether, or thioether bond; or is attached to the phosphate or carbohydrate by a bond that is an ester, thioester, amide, ether, or thioether. Alternatively, a cyanine dye may be bound to the nucleic acid by chemical post-modification, such as with platinum reagents, or using a photoactivatable molecule such as a conjugated psoralen.

(IV) Uses of the Fluorescent Cyanine Dyes

The cyanine dyes of the invention are useful in many applications including those described for other cyanine dyes in U.S. Pat. Nos. 7,172,907; 5,268,486; and U.S. Patent Application Nos. 20040014981; and 20070042398, each of which is incorporated herein by reference. For example, fluorescent dyes may be used in imaging with techniques such as those based on fluorescence detection, including but not limited to fluorescence lifetime, anisotropy, photoinduced electron transfer, photobleaching recovery, and non-radioactive transfer. The fluorescent cyanine dyes, as such, may be utilized in all fluorescent-based imaging, microscopy, and spectroscopy techniques including variations on such. In addition, they could also be used for photodynamic therapy and in multimodal imaging. Exemplary fluorescence detection techniques include those that involve detecting fluorescence generated within a system. Such techniques include, but are not limited to, fluorescence microscopy, fluorescence activated cell sorting (FACS), fluorescent flow cytometry, fluorescence correlation spectroscopy (FCS), fluorescence in situ hybridization (FISH), multiphoton imaging, diffuse optical tomography, molecular imaging in cells and tissue, fluorescence imaging with one nanometer accuracy (FIONA), free radical initiated peptide sequencing (FRIPs), and second harmonic retinal imaging of membrane potential (SHRIMP), as well as other methods known in the art.

Alternatively, the fluorescent cyanine dyes can be used as markers or tags to track dynamic behavior in living cells. In this regard, fluorescence recovery after photobleaching (FRAP) can be employed in combination with the subject fluorescent cyanine dyes to selectively destroy fluorescent molecules within a region of interest with a high-intensity laser, followed by monitoring the recovery of new fluorescent molecules into the bleached area over a period of time with low-intensity laser light. Variants of FRAP include, but are not limited to, polarizing FRAP (pFRAP), fluorescence loss in photo-bleaching (FLIP), and fluorescence localization after photobleaching (FLAP). The resulting information from FRAP and variants of FRAP can be used to determine kinetic properties, including the diffusion coefficient, mobile fraction, and transport rate of the fluorescently labeled molecules. Methods for such photo-bleaching based techniques are described in Braeckmans, K. et al., Biophysical Journal 85: 2240-2252, 2003; Braga, J. et al., Molecular Biology of the Cell 15: 4749-4760, 2004; Haraguchi, T., Cell Structure and Function 27: 333-334, 2002; Gordon, G. W. et al., Biophysical Journal 68: 766-778, 1995, which are all incorporated herein by reference in their entirety.

Other fluorescence imaging techniques are based on non-radioactive energy transfer reactions that are homogeneous luminescence assays of energy transfer between a donor and an acceptor. Such techniques that may employ the use of the subject fluorescent dyes include, but are not limited to, FRET, FET, FP, HTRF, BRET, FLIM, FLI, TR-FRET, FLIE, smFRET, and SHREK. These techniques are all variations of FRET.

The subject fluorescent dyes may be used as biosensors such as a $Ca^{2+}$ ion indicator; a pH indicator; a phosphorylation indicator, or an indicator of other ions, e.g., magnesium, sodium, potassium, chloride and halides. For example, biochemical processes frequently involve protonation and deprotonation of biomolecules with concomitant changes in the pH of the milieu. Substitution at the meso-position with different pH-sensitive groups generates a variety of NIR fluorescent pH sensors with different pKa's. To be effective, the substituents at the meso-position will be in extended π-conjugation with the cyanine fluorophore core to effect marked spectral changes in response to different pH environments.

DEFINITIONS

The term "acyl," as used herein alone or as part of another group, denotes the moiety formed by removal of the hydroxyl group from the group—COOH of an organic carboxylic acid, e.g., RC(O)—, wherein R is R', $R_1O$—, $R'R_2N$—, or $R_1S$—, $R_1$ is hydrocarbyl, heterosubstituted hydrocarbyl, or heterocyclo and $R_2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

Unless otherwise indicated, the alkenyl groups described herein are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

As used herein, the term "functional group" includes a group of atoms within a molecule that is responsible for certain properties of the molecule and/or reactions in which it takes part. Non-limiting examples of functional groups include, alkyl, carboxyl, hydroxyl, amino, sulfonate, phosphate, phosphonate, thiol, alkyne, azide, halogen, and the like.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, ketals, acetals, esters and ethers.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, carbocycle, aryl, heterocyclo, alkoxy, alkenoxy, alkynoxy, aryloxy, hydroxy, protected hydroxy, keto, acyl, acyloxy, nitro, amino, amido, nitro, cyano, thiol, ketals, acetals, esters and ethers.

The term "linking group" includes a moiety on the compound that is capable of chemically reacting with a functional group on a different material (e.g., biomolecule) to form a linkage, such as a covalent linkage. See R. Haughland, *The Handbook—A Guide to Fluorescent Probes and Labeling Technologies*, 9th Edition, Molecular probes, Inc. (1992). Typically, the linking group is an electrophile or nucleophile that can form a covalent linkage through exposure to the corresponding functional group that is a nucleophile or electrophile, respectively. Alternatively, the linking group is a photoactivatable group, and becomes chemically reactive only after illumination with light of an appropriate wavelength. Typically, the conjugation reaction between the dye bearing the linking group and the material to be conjugated with the dye results in one or more atoms of the linking group being incorporated into a new linkage attaching the dye to the conjugated material.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various embodiments of the invention.

Example 1

Synthesis of C—C Containing Dyes

The precursor chloro cyanine dyes 1a-1c (FIG. 3) utilized in the C, C coupling reactions can be efficiently synthesized via condensation reactions of a heterocyclic base with Vilsmeier-Haack reagents. Thus, separate reactions of chloro-substituted benz[e]indolium dyes 1a-1c (FIG. 3) with 4-B(OH)$_2$C$_6$H$_4$—CO$_2$H in the presence of Pd(PPh$_3$)$_4$ using aqueous reaction conditions proceeded efficiently to afford the desired dyes 2a-2c (FIG. 3) in 68-83% yields, respectively.

Figure 3:
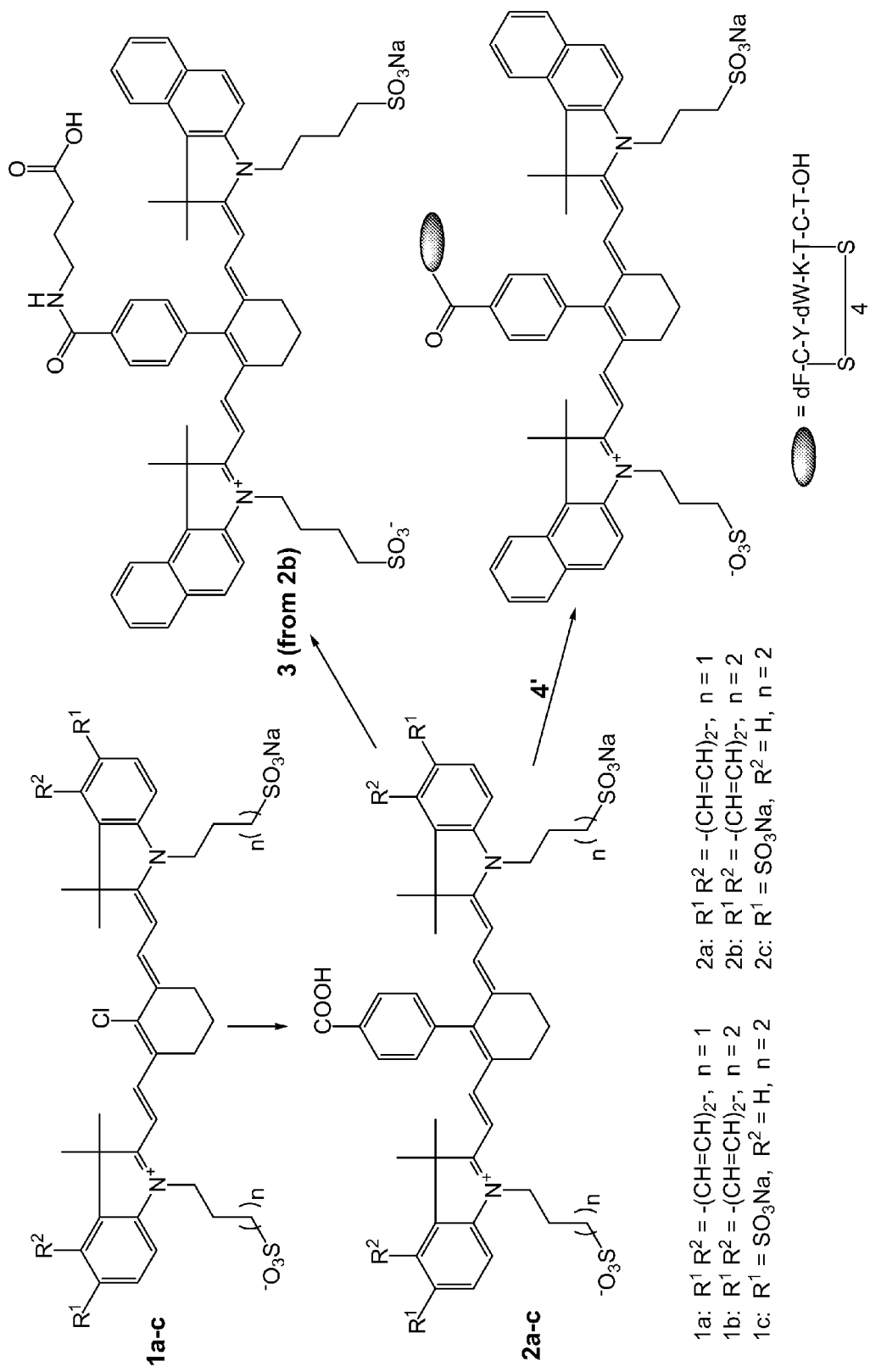
FIG. 3 depicts the synthesis and peptide labeling reactions of the new highly fluorescent, monofunctional, water-soluble heptamethine cyanine dyes containing a robust C—C bond at the central position of the chromophore by the Suzuki-Miyaura method.
Figure 4:
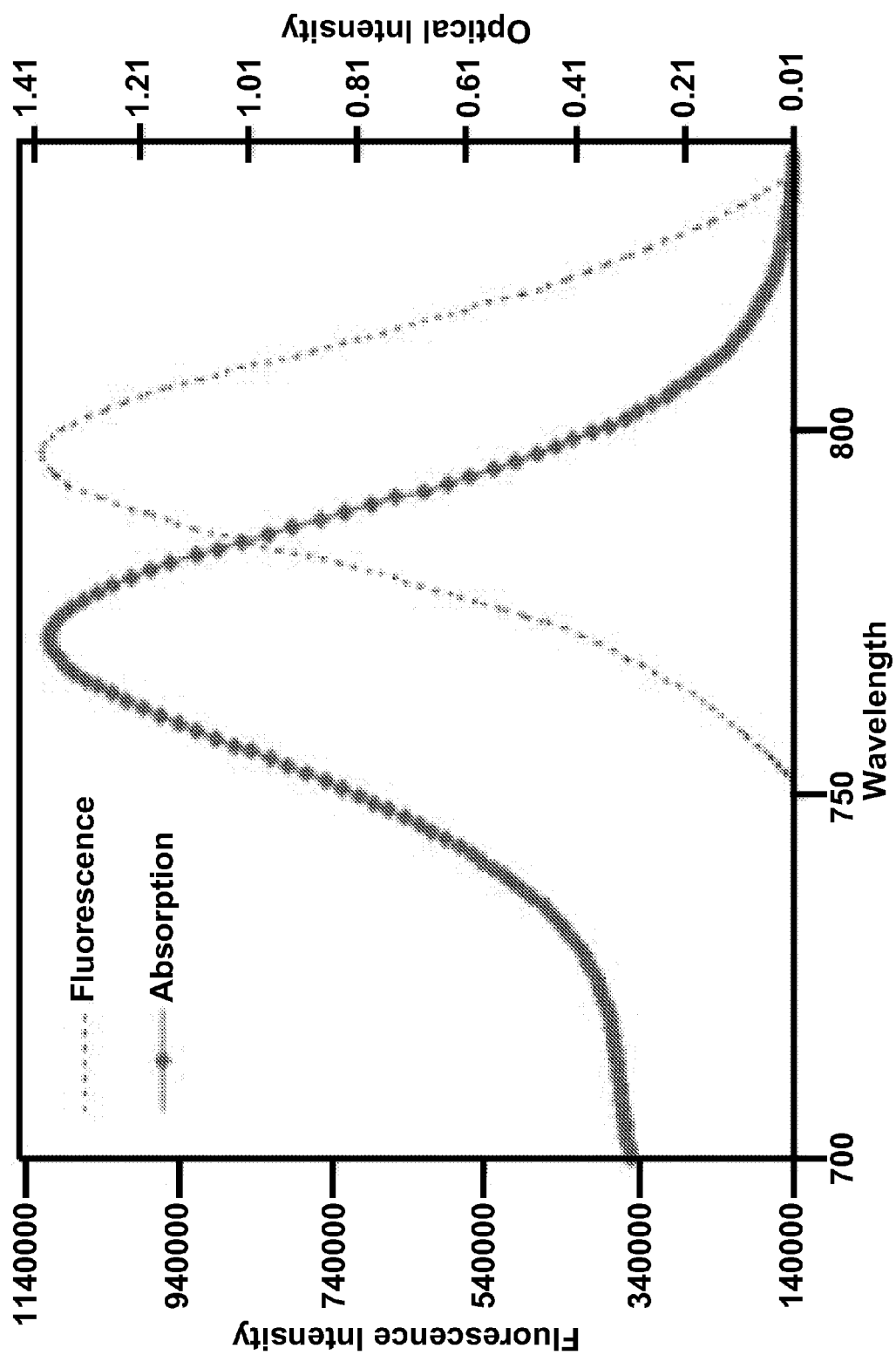
FIG. 4 graphically illustrates the absorption and emission spectra of dye 2c in 20% aqueous DMSO solution.

Synthesis of Chloro Dyes 1a-1c of FIG. 3. Condensation of heterocyclic salts and dianil was conducted in a 1:1 mixture of ethanol and acetic anhydride in the presence of sodium acetate by using a general procedure. The compounds were recrystallized from methanol/ether.

Synthesis of Cyanine Dyes 2a-2c of FIG. 3. Precursor chloro dyes 1a-1c (1.0 mmol) and 4-carboxyphenylboric acid (1.8 mmol) in H$_2$O was heated under reflux in the presence of Pd(PPh$_3$)$_4$ (0.065 mmol) for 6-9 h. The reaction progress was monitored by visible/near infrared spectroscopy for aliquots diluted with methanol until absorption of the starting chloro cyanine disappeared. The reaction mixture was then cooled to room temperature, and H$_2$O was removed in vacuo. The solid was isolated by precipitation with MeOH/acetone, and the precipitate was further washed with acetone. The dye 2c obtained was additionally crystallized from EtOH.

Characteristics of Dye 2a of FIG. 3. Yield 68%. $^1$H NMR: δ 1.41 (s, 12H), 2.04 (m, 6H), 2.59 (t, J=6 Hz, 4H), 2.78 (t, J=6 Hz, 4H), 4.42 (t, J=7 Hz, 4H), 6.46 (br d, J=14 Hz, 2H), 7.14 (br d, J=14 Hz, 2H), 7.45 (d, J=9 Hz, 2H), 7.47 (t, J=8 Hz, 2H), 7.57 (t, J=8 Hz, 2H), 7.78 (d, J=9 Hz, 2H), 8.01 (m, 6H), 8.24 (d, J=8 Hz, 2H). $\lambda_{max}$ (in 25% aqueous DMSO): 800 nm (ε240 000 M$^{-1}$ cm$^{-1}$). $\Phi_F$ (MeOH): 0.088. ESI-MS (negative matrix), m/z: 883 (M$^+$-Na, 100%).

Characteristics of Dye 2b of FIG. 3. Yield 83%. $^1$H NMR: δ 1.40 (s, 12H), 1.76 (m, 8H), 2.01 (m, 2H), 2.55 (m, 4H), 2.76 (m, 4H), 4.26 (m, 4H), 6.32 (br d, J=14 Hz, 2H), 7.13 (br d, J=14 Hz, 2H), 7.46 (m, 4H), 7.58 (t, J=8 Hz, 2H), 7.73 (d, J=9 Hz, 2H), 8.01 (m, 6H), 8.25 (d, J=8 Hz, 2H). $\lambda_{max}$ (in 25% aqueous DMSO): 800 nm (ε240 000 M$^{-1}$ cm$^{-1}$). $\Phi_F$ (MeOH): 0.092. MS-ESI, m/z: 913 (M$^+$-Na, 100%).

Characteristics of Dye 2c of FIG. 3. Yield 73%. $^1$H NMR: δ 1.10 (s, 12H), 1.58 (m, 2H), 1.72 (m, 4H), 2.45 (t, J=6 Hz, 4H), 2.72 (m, 4H), 3.32 (t, J=6 Hz, 4H), 4.11 (m, 4H), 6.28 (br d, J=14 Hz, 2H), 7.02 (br d, J=14 Hz, 2H), 7.30 (d, J=8 Hz, 4H), 7.41 (d, J=8 Hz, 2H), 7.60 (d, J=8 Hz, 2H), 7.61 (s, 2H), 8.19 (d, J=8 Hz, 2H). $\lambda_{max}$ (in 25% aqueous DMSO): 770 nm (ε220 000 M$^{-1}$ cm$^{-1}$). $\Phi_F$ (MeOH): 0.100. ESI-MS (negative matrix), m/z: 971 (M$^+$-3Na, 100%).

Example 2

Spectral Properties of Dyes 2a-c of FIG. 3

Figure 2:
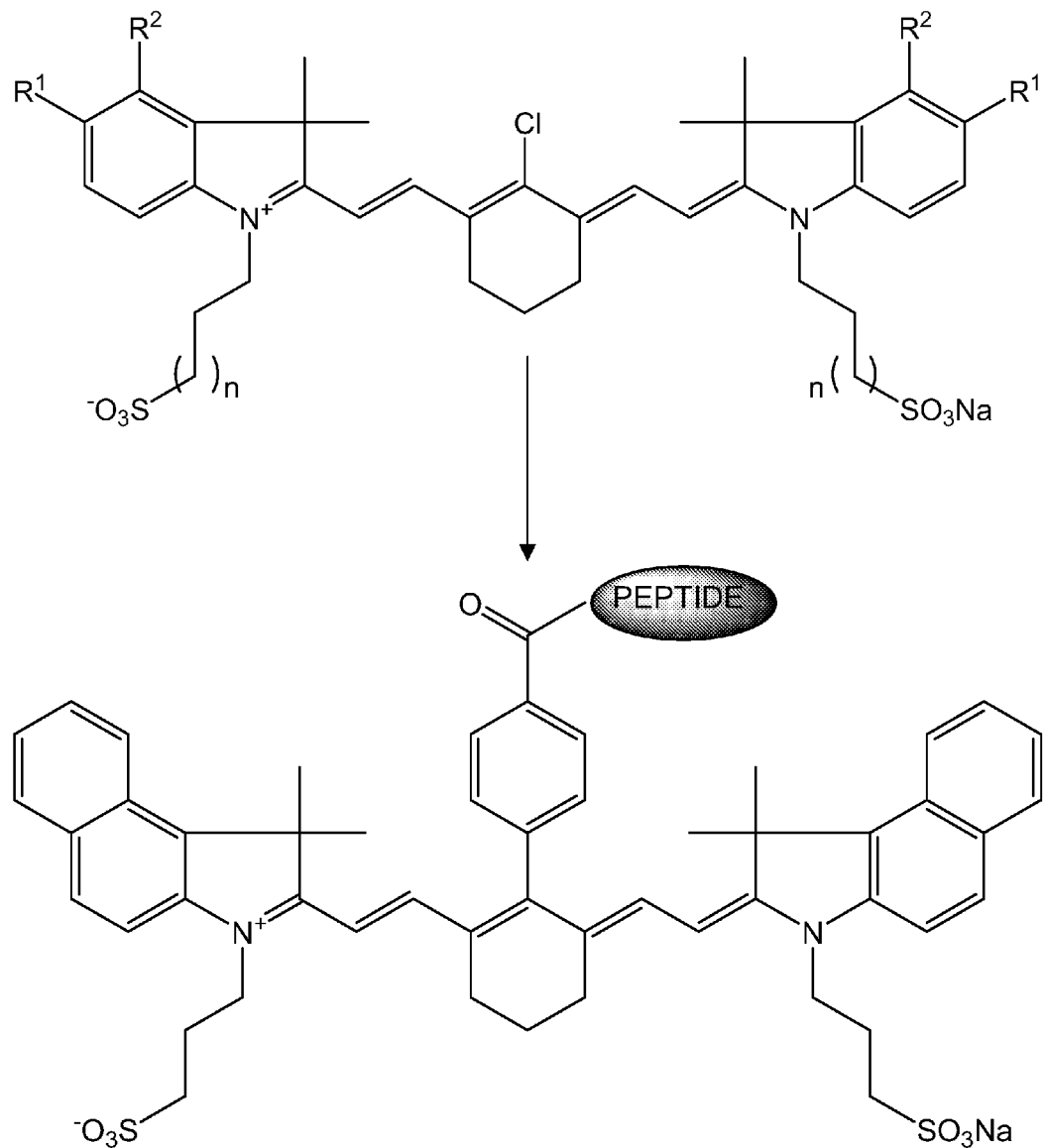
FIG. 2 illustrates the reaction replacing the meso-chlorine atom of heptamethine cyanine dyes with a robust carboxy-functionalized aryl moiety producing highly fluorescent, monofunctional, water-soluble heptamethine cyanine dyes.

Spectral properties of the newly synthesized dyes 2a-c are shown in Table 1 in comparison to those of indocyanine green (ICG). The absorption spectra of these dyes show a characteristic band broadening, which is typical of heptamethine dyes with the absorption maxima in the range of 770-800 nm. They exhibit a hypsochromic shift (~20 nm) from their parent chloro dyes 1a-c (795-820 nm), indicating a direct interaction of the aryl group with the chromophore system. Their exceptionally high molar absorptivities of 240,000 M$^{-1}$ cm$^{-1}$ for dyes 2a,b and 220,000 M$^{-1}$ cm$^{-1}$ for dye 2c exceed those of many organic dyes. Although the maximum emission wavelengths vary from 770 to 811 nm with small Stoke's shifts of 10-15 nm, the broad emission bands allow flexibility in the choice of excitation and fluorescence wavelengths in analytical and biological assays. The relative fluorescence quantum yields of dyes 2a-c measured in MeOH using ICG as a standard show moderate improvement with the values in the range of 0.088-0.10 compared to 0.078 for ICG. Also noteworthy is the fact that the relatively low fluorescence quantum yields of these compounds are compensated by their very high molar absorptivities, as reflected in their impressive brightness (Table 1). The brightness or fluorescence intensity per dye molecule, which is the product of the fluorescence quantum yield and molar absorptivity, is a useful index to predict the sensitivity of detecting small amounts of the fluorescent probes, especially in heterogeneous media such as cells and tissues. The representative absorption and fluorescence spectra of these dyes are shown in FIG. 2.

TABLE 1

Comparative Spectral Properties of 2a-c and ICG in Methanol.

| Compd | $\lambda_{max, abs}$ (nm) | $\lambda_{max, em}$ (nm) | ε (M$^{-1}$cm$^{-1}$) | $\Phi_F^a$ | $\Phi_B^b$ |
|---|---|---|---|---|---|
| 2a | 800 | 811 | 240000 | 0.088 | 1.3 |
| 2b | 800 | 811 | 240000 | 0.092 | 1.4 |
| 2c | 770 | 785 | 220000 | 0.10 | 1.4 |
| ICG | 785 | 807 | 204000 | 0.078$^c$ | 1 |

$^a$Relative fluorescence quantum yield.
$^b$Relative brightness referenced to ICG.
$^c$Quantum yield standard.

UV-Vis and Fluorescent Spectroscopic Analysis. Stock solutions (3.0 mM) of the dye and its conjugates were prepared by dissolving them in DMSO. UV-Vis and fluorescence measurements were carried out by sequentially adding 0.5-2.0 μl aliquots of the stock solutions via a micropipet into 3 mL of 20% aqueous DMSO solution in a quartz cuvette and stirring for equilibration prior to acquiring the spectra. The molar extinction coefficient was obtained using Beer's law at 0.1-0.6 μM concentration of the dye. The relative fluorescence quantum yield was determined using the equation:

$$\Phi_{F(x)} = (A_s/A_x)(F_x/F_s)(n_x/n_s)^2 \Phi_{F(s)}$$

where $\Phi_{F(X)}$ is the fluorescence quantum yield, A is the absorbance, F is the area under the emission curve, n is the refractive index of the solvents used in measurement, and the subscripts s and x represent the standard and unknown, respectively. Indocyanine green (ICG) was used as a reference standard.

Example 3

Conjugation Efficiency of Dyes

Figure 6:
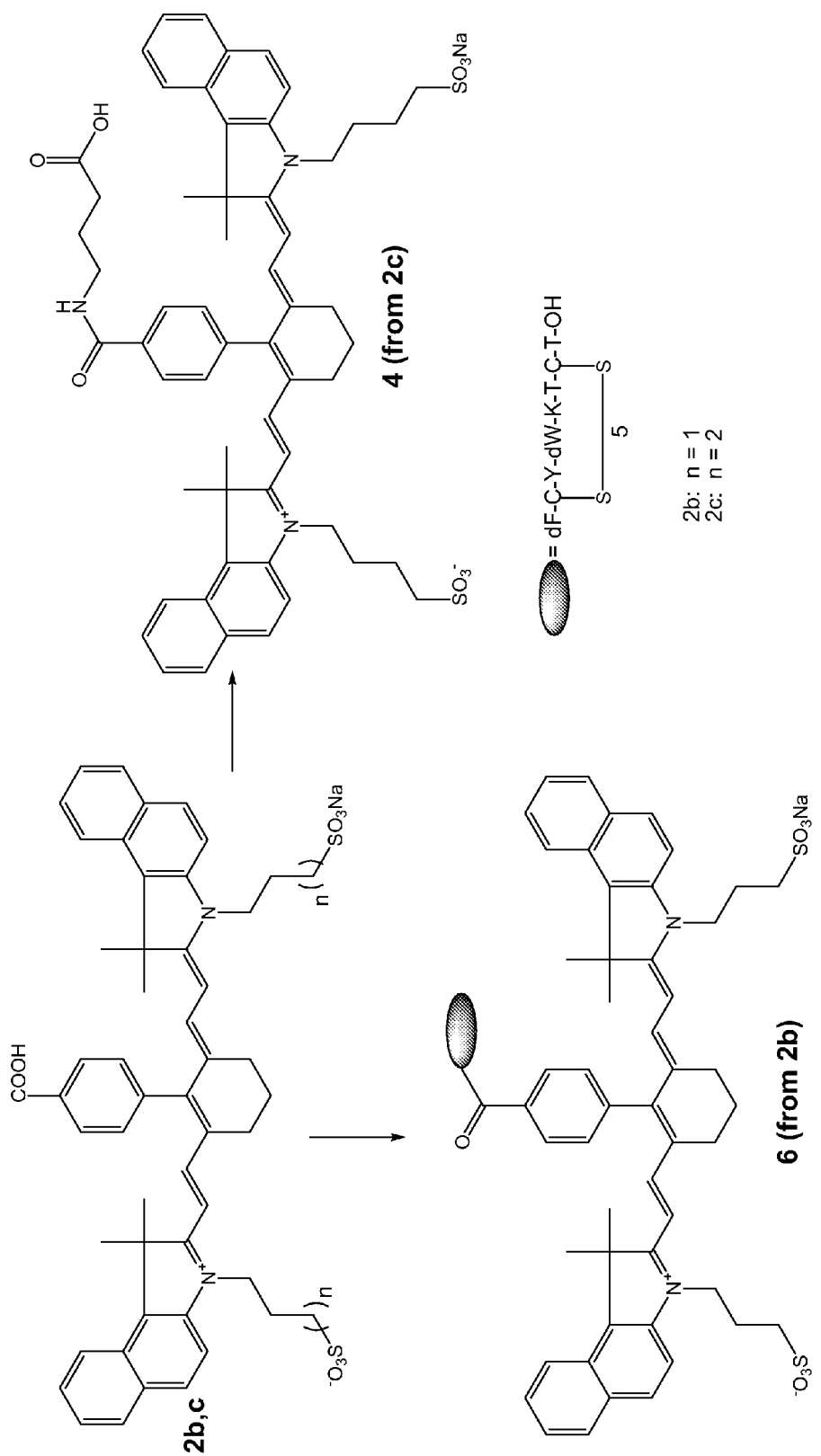
FIG. 6 depicts a schematic of the conjugation of heptamethine cyanine dyes having robust C—C bond at the central position of the chromophore. The reaction conditions include: (i) (a) ε-Ahx/HBTU/HOBt/DMF-MeOH, (b) TFA; and (II) (a) HBTU/HOBt/DMF-MeOH, (b) TFA.

The conjugation efficiency of dyes 2a-c (FIG. 3) was evaluated via solid-phase chemistry by reacting 2b with ε-aminohexanoic acid (ε-Ahx) as illustrated in FIG. 6. The N-Fmoc-protected ε-Ahx was coupled to a Rink amide resin by standard Fmoc peptide chemistry. After removing the F-moc with 20% piperidine in DMF, treatment of 2b with the resin-bound ε-Ahx in the presence of N-hydroxylbenzotriazole (HOBt), 2-(1-H-benzotriazole-1-yl)-1,1,1,3-tetramethyluronium hexafluorophosphate (HBTU), and DIEA gave the desired product. The absorption maximum of the compound was retained at 803 nm after TFA-mediated cleavage from the resin and HPLC purification. This result suggests that compounds 2a-c (FIG. 3) possess excellent chemical stabilities that are needed for solid-phase peptide synthesis and harsh cleavage conditions.

To further demonstrate the feasibility of labeling biologically relevant molecules with dye 2b, a somatostatin receptor-avid octapeptide (octreotate 5') was utilized. Previous studies have shown that targeting this receptor with fluorescent- or radiolabeled peptides facilitates the visualization of tumors in humans and small animals. Octreotate was assembled on a solid support using Wang resin, and the N-terminal Fmoc was removed. The hydrophilic dye was suspended in DMF, and drops of MeOH were added until a clear solution was obtained. Subsequent activation with a mixture of HOBt/HBTU coupling reagents and reaction with the amino group of the peptide on the solid support afforded the desired dye-peptide conjugate 6 after removal of all side-chain amino acid protecting groups and cleavage from the resin using TFA. The new dye peptide conjugate was purified by HPLC and characterized. The absorption and fluorescence spectra of the dye in compound 6 (FIG. 6) were practically unchanged, demonstrating the feasibility of using these dyes to label biomolecules.

Synthesis of Cyanine-Octreotate 5 from 2a (FIG. 3). The resin-bound peptide was assembled starting from Wang resin based on conventional F-moc chemistry. To the resulting resin-bound peptide was added a solution of the cyanine dye (3 equiv) preactivated with HBTU/HOBt (3 equiv) in DMF/MeOH. The resulting mixture was mixed for 5 h at room temperature. The resin was then washed with DMF, MeOH, and DCM and cleaved with a cleavage mixture consisting of 95% TFA, 2.5% phenol, 2.5% thioanisole, and 5% H$_2$O for 90 min. The resin was filtered, and the filtrate was precipitated in cold tert-butyl methyl ether and purified by semipreparative HPLC to afford the dyeoctreotate conjugate. ESI-MS, calcd m/z: 1916. Observed for ESI-MS, m/z: 1916 (M$^+$-Na, 100%).

What is claimed is:
1. A compound of the formula of a fluorescent cyanine dye selected from the group consisting of

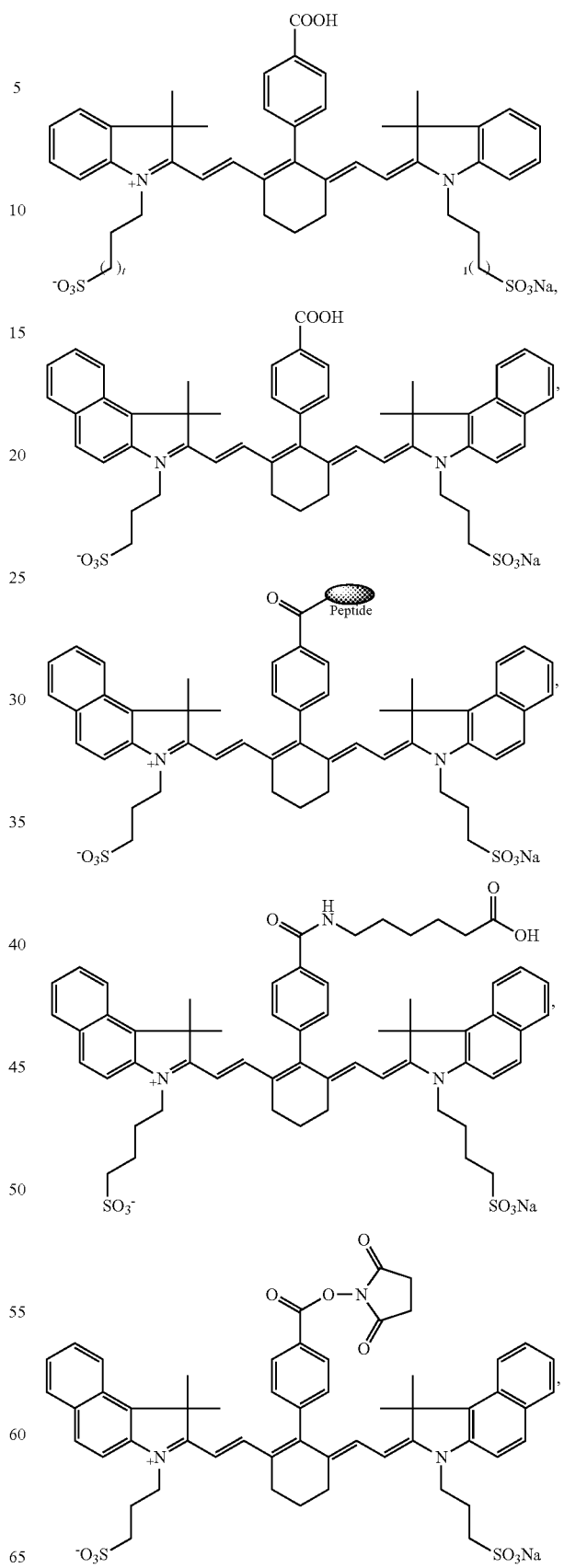

-continued

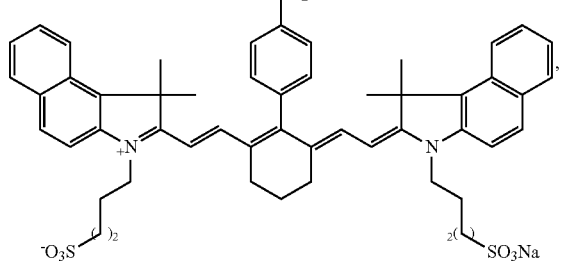

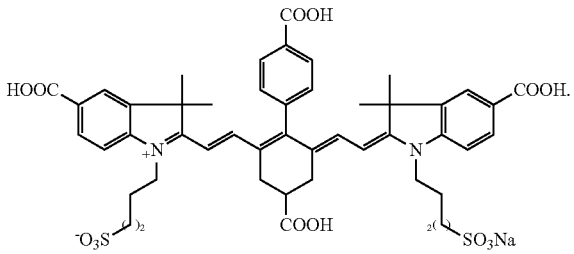

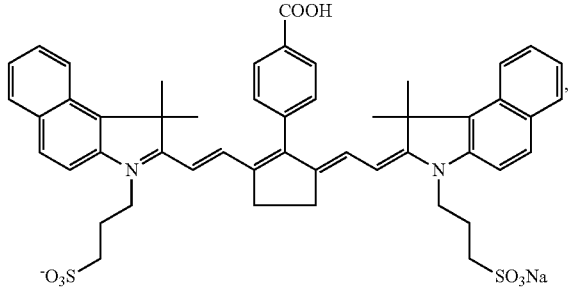

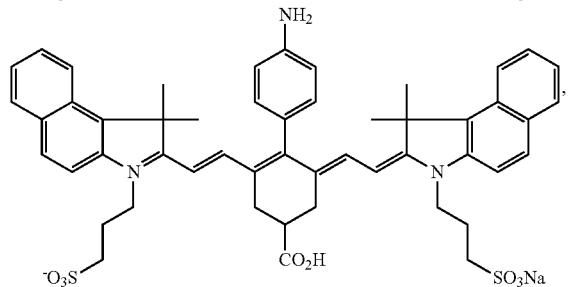

2. The compound of claim 1, further comprising a biomolecule conjugated to the fluorescent cyanine dye.

3. The compound of claim 2, wherein the biomolecule is selected from the group consisting of an antigen, an antibody, a drug, a vitamin, and a small molecule.

4. The compound of claim 2, wherein the biomolecule is selected from the group consisting of a peptide, a nucleic acid, a carbohydrate, and a lipid.

5. The compound of claim 4, wherein the biomolecule is a peptide.

6. A process for producing a fluorescent cyanine dye, the process comprising:
 a. combining a meso-chloro substituted heptamethine cyanine dye, 4-carboxyphenylboric acid, and water;
 b. heating the combination under reflux in the presence of Pd(PPh$_3$)$_4$;
 c. isolating the resulting fluorescent cyanine dye.

* * * * *